United States Patent [19]
Schwartz et al.

[11] Patent Number: 6,098,205
[45] Date of Patent: *Aug. 8, 2000

[54] GOGGLES WITH PLIABLE AND RESILIENT SEALING PAD

[76] Inventors: Alan N. Schwartz, 19211 93$^{rd}$ PLW, Edmonds, Wash. 98020; Thomas D. Theisen, 14012 Riviera Pl. NE., Seattle, Wash. 98125

[ * ] Notice: Under 35 U.S.C. 154(b), the term of this patent shall be extended for 431 days.

[21] Appl. No.: 08/794,154

[22] Filed: Feb. 3, 1997

Related U.S. Application Data

[63] Continuation of application No. 08/377,257, Jan. 23, 1995, abandoned.

[51] Int. Cl.$^7$ ........................................ A61F 9/02
[52] U.S. Cl. ........................................ 2/428; 128/206.24
[58] Field of Search ................ 2/428, 429, 430, 2/411, 439, 452, 9, 447; 128/206.24, 206.25, 206.26

[56] References Cited

U.S. PATENT DOCUMENTS

| | | | |
|---|---|---|---|
| 3,725,953 | 4/1973 | Johnson et al. | 2/428 |
| 4,707,863 | 11/1987 | McNeal | 2/439 X |
| 5,093,940 | 3/1992 | Nishiyama | 2/441 |
| 5,331,691 | 7/1994 | Runckel | 2/452 X |
| 5,334,646 | 8/1994 | Chen | 2/411 X |

*Primary Examiner*—Peter Nerbun
*Attorney, Agent, or Firm*—Thomas D. Theisen

[57] ABSTRACT

The goggles (10) include a frame (12) having a transparent portion adapted to cover at least one of the users eyes and a sealing pad (14) adjacent to the frame, comprising a compliant and resiliently deformable gelatinous elastomer suitable to conform under pressure to form a substantially airtight seal between the frame (12) and at least a portion of the user's face adjacent to the sealing pad (14).

2 Claims, 3 Drawing Sheets

GOGGLES WITH PLIABLE AND RESILIENT SEALING PAD

This application is a continuation application of application Ser. No. 08/377,257, filed on Jan. 23, 1995, now abandoned.

FIELD OF THE INVENTION

The invention relates to goggles, specifically to such goggles as might be used for swimming or isolation of the eyes from the outside environment.

BACKGROUND OF THE INVENTION

Goggles are commonly used to separate or isolate the eyes and face of the user from the nearby environment. For example, swimming goggles are utilized to separate and protect the eyes from water thereby allowing the swimmer to see clearly within and find a path through the water. Other goggles, such as protective goggles, are utilized to prevent exposure of the user's eyes to toxins or contaminated material, such as blood or harmful gases or materials. Goggles may also be used to protect the eyes from harmful or undesirable environmental conditions, such as cold or dry air or sand or dust in the air. Goggles may also be used to retain a particular fluid or gas near the eyes.

Traditionally, goggles have been made with a rigid or semi-rigid frame, which was directly compressed against the skin of the face by use of an elastic strap extending around the user's head. Frames were poorly compliant and did not conform well to the user's face at a comfortable pressure. This often resulted in an incomplete seal that was not watertight. In order to create a better seal, the goggles could be more firmly compressed against the face. This created discomfort and irritation to the face, facial bones, and delicate underlying blood vessels.

The problem with rigid or semi-rigid frames was partially solved by utilizing softer frame materials and by placing a pad or gasket between the frame and user's face. These pads were made with various materials, such as rubber or plastic, which were softer and more compliant than the frame materials.

There are, however, problems with existing goggles that utilize a pad or gasket. Existing solid pads have limited ability to conform to the variations in the human facial bone structure. To create a watertight seal, large compressive forces often must be applied to the frame to force the existing solid pad against the user's face. In some individuals, the pressure and resulting compression can be tolerated, but in others their skin is too delicate to comfortably withstand the large compressive force required. For these individuals, discomfort precludes their ability to successfully use this form of goggle. For other individuals, the bone structure is not compatible with the shape of a goggle and water and air leaks occur even with high compressive forces.

Less rigid pads or gaskets made of foam rubber or other foam plastics have also been used. These pads consist of plastic or rubber material that contains numerous tiny air spaces and can be readily compressed at low pressure. The foam pad is better able to conform to the facial bone structure. Although foam pads are generally an improvement over existing solid pads, there is a limited capacity for the foam pads to conform to the delicate facial skin and bone structures. Moreover, the compressive forces are not symmetrically distributed throughout the pad. This results in pressure points where prominent facial bones meet the pad.

If the pad does not conform fully to the contour of the facial bones, the result is a leak where air, water or other material may pass between the pad and the user's face. Such leaks can often, but not always, be reduced or eliminated by increasing the pressure applied by the frame upon the face. If the foam is thick enough and enough pressure is applied, the foam pad will usually fill in the gaps between the face and frame. When tightly compressed against the face, however, the foam pad takes on more of the characteristics of a soft rubber of plastic pad. Therefore, these foam pads suffer from many of the same limitations of discomfort and damage to the facial skin and blood vessels as do the more rigid solid pads.

In addition, because foam has air pockets or pores, it cannot be fully cleaned after each usage. As a result, bacteria and fungus grow in the air pockets in the foam. Such bacterial and fungal growth can serve as a source of eye and skin infections and can be a hygiene and health risk.

Attempts have been made to vary the shape and size of the goggle frame in order to obtain a more successful seal with the user's face. This has been useful for some individuals but because of the human variability in facial bone structure, this is unsuccessful for many individuals. There are a limited number of shapes that can be cost-effectively manufactured and these shapes do not necessarily conform to the numerous variations in bone and facial structure.

SUMMARY OF THE INVENTION

The present invention provides goggles for isolation of the user's eyes from the outside environment, including the frame having a transparent portion or portions adapted to cover the user's eyes and a sealing pad which forms a substantially airtight seal between the frame and the user's face adjacent to the sealing pad. The sealing pad includes a compliant and resiliently conformable gelatinous elastomer which forms an airtight seal to the user's face under slight to moderate pressure.

The sealing pad of the invention more readily conforms to the numerous variations in human facial bone structure when in use and returns to its original shape after use. The material of the pad will, for example, conform to the facial bone structure and form an airtight or watertight seal with less pressure or compressive force than is required for solid or semisolid frame without such a pad.

The material of the pad will also conform to the facial bone structure by distributing the compressive force throughout a larger portion of the pad. As a result, facial prominence will not become pressure points since the pressure is more evenly distributed within the transition pad itself. This has a potential to reduce irritation and discomfort of goggles to individuals with sensitive skin. It also reduces the discomfort to an individual who has areas of bone prominence in or near the eye socket.

Because the pad is soft and compliant, it can also more accurately contour and conform to the facial structures and have the advantage of creating a more effective watertight seal than solids or foam. For example, these goggles can therefore keep water out more effectively. They also can, because of the better seal, better protect the eyes from dangerous environmental exposures, toxins, chemicals, gases, or contaminated blood. Because the pad is soft and compliant it can also expand and contract and be designed to absorb shock more effectively, thus protecting the eye and the eye socket from direct compressive blow, such as might occur with sporting injuries.

Because of the pad, the outer frame can be created in many shapes. It can be designed in forms that conform to the eye socket, or it can extend outside of the eye socket. The advantage of creating a frame that is not restricted to the eye socket is that the skin is thicker and less delicate over the cheek and eyebrow than it is immediately over and around the eye, resulting in greater comfort and less damage to the delicate skin of the eye. Because of the pad, the goggles require less compressive force and the compressive force need not be applied perpendicular to the frame. Thus, a non-rigid frame can be used.

Because the pad does not rely upon air holes for its malleability and contouring as is necessary with foam pads, the pad can be made and formed to be resistant to bacterial or fungal growth. A membrane that is biocompatible with the skin and which is bacterial and fungal resistant can also be placed around the transition pad. This can provide an added safety element to the pad.

The goggles can be constructed such that the components can be interchangeable and replaceable: that is, the frame, the eyepiece, the pads, and the straps could all be replaceable if damaged. This allows the user and manufacturer to produce components to the goggles that can be repaired, replaced, changed for design purposes, all at a cost less than replacing the entire goggle.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
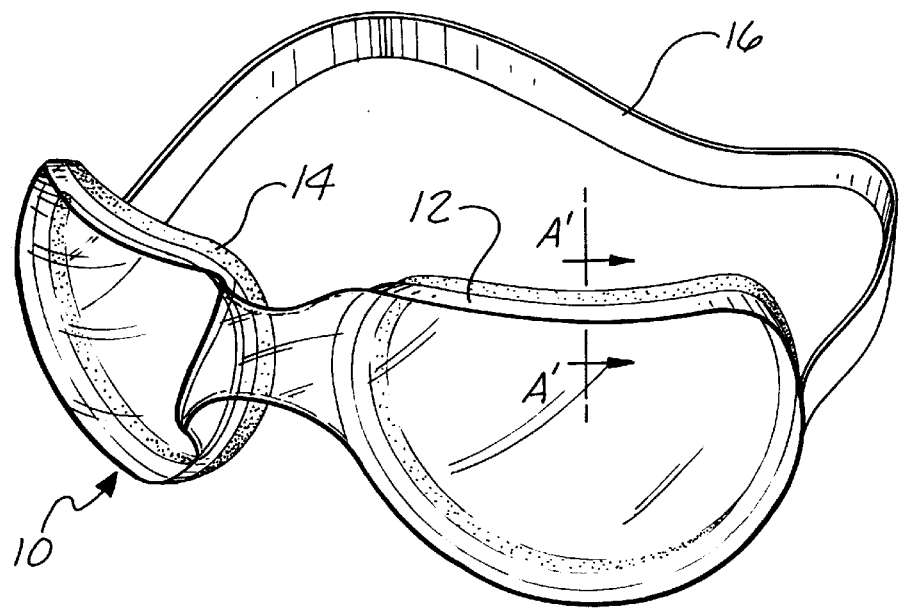
FIG. 1 shows a pictorial view of the goggles in accordance with the present invention.

A goggle 10 constructed in accordance with the present invention is shown in FIG. 1. The goggles include a frame 12 having a portion to cover, or otherwise isolate from the outside environment, one or both of the user's eyes. A portion of the frame 12 is transparent, meaning that it allows some light to pass from the outside environment to the user's eye. The transparent portion of the frame 12 may transmit all wavelengths of light, selectively block or attenuate certain wavelengths of light or attenuate all wavelengths of light.

In the preferred embodiment of the invention, the frame 12 is made of plastic or other material which is relatively rigid, yet soft enough to conform to the overall shape of the user's face and head. The frame may be made of various materials, such as rigid poly vinyl chloride, or acrylic lenses surrounded by a flexible poly vinyl chloride perimeter, for example. However, this invention is consistent with, and includes, virtually any type of frame 12 which can isolate or protect the user's eyes from the outside environment and includes, for example, rigid pieces of plastic designed to fit and generally conform to the shape of the orbit of the user's eye socket or a thin film of flexible material sized to extend beyond and fit outside the orbits of the user's eye socket.

The goggles also include a sealing pad 14 between the frame 12 and the user's face which forms a substantially airtight seal between the frame 12 and the user's face. In the preferred embodiment, the sealing pad 14 is a strip of material with a cross section width and height of between approximately one-eighth inch and approximately one-half inch. The sealing pad 14 is near at least a portion of the perimeter of the frame 12, and in the preferred embodiment entirely surrounds each of the user's eyes near perimeter of the frame. An optional strap 16 is used in the preferred embodiment to apply slight pressure to hold the sealing pad 14 against the user's face.

The sealing pad 14 is configured so that when it is in use it forms a continuous and substantially airtight seal with the user's face along at least a portion of the frame 12. The sealing pad 14 is made from a gelatinous elastomer which is both complaint and yet resiliently deformable. Specifically, the gelatinous elastomer must be sufficiently compliant to conform to the irregularities of the user's face when slight to moderate pressure is applied to the pad 14. If the gelatinous elastomer is too hard or rigid, it will not form a substantially air-tight seal to the user's face without the application of undue pressure resulting in pain or discomfort to the user. On the other hand, if the gelatinous elastomer is too soft, it is possible that in forming a substantially air-fight seal the elastomer will be forced out from between the frame 12 and the user's face at certain locations, again, possibly causing pain or discomfort to the user or impinging on the user's eye.

The gelatinous elastomer also needs to deform in a substantially resilient manner as pressure is applied to the sealing pad 14. If the gelatinous elastomer is permanently deformed to a substantial extent when sufficient pressure is applied to form a substantially air-tight seal between the pad 14 and the user's face, or if the elastomer does not return to its approximate original shape following the removal of such pressure, then the goggles may not fit as well when they are used again. For example, if the goggles are used by a different user or at a slightly different location on the original user's face, any substantial permanent deformation of the elastomer may adversely affect the performance of the sealing pad 14.

Various gelatinous elastomers were evaluated for use in the sealing pad 14. The preferred embodiment of the invention is made from the same material used in the Kitecko Ultrasound Standoff Pad 3520 and 3530, manufactured by 3M Corporation of St. Paul, Minn. Specific information regarding the composition of such material is not available from 3M Corporation. Various soft urethane gels and soft silicone gels were also found to be acceptably compliant and deformable, but may require the use of a membrane to prevent damage to the user's skin.

Figure 2:
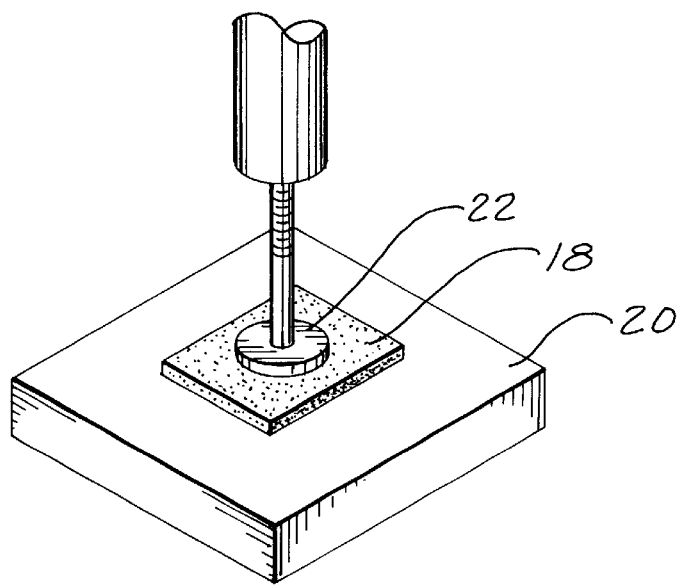
FIG. 2 shows a partial pictorial view of the apparatus used to identify whether a particular gelatinous elastomer is desirable for use in this invention.

It appears that there is no general accepted test or method to measure how compliant or deformable a gelatinous elastomer is. The following method and procedure illustrated in FIG. 2 was used to help identify whether a particular gelatinous elastomer is desirable for use in the sealing pad of this invention. A sample strip 18 of the elastomer approximately 0.3 of an inch high, 0.5 of an inch wide, and 1.0 inches long was placed upon a scale 20 that measures the downward force exerted by the strip 18 of gelatinous elastomer.

A rigid circular disk 22 having a diameter of 0.43 inches was placed so that it just contacted the top surface of the sample strip 18, and the scale 20 was zeroed. The circular disk 22 was then moved downward in 0.025 inch increments until the sample strip 18 ceased to be resiliently deformable, i.e., until the sample started to tear under the circular disk 22. For each incremental 0.025 inch deflection, the total downward force in grams measured by the scale 20 was recorded. Sample strips of gelatinous elastomers of varying compliancy and resiliency (hereinafter samples A, B, D and E) made from common household edible gelatin, along with a sample cut from the Kitecko Ultrasound Standoff pad (sample C) were tested. The downward force, measured on the scale 20 in grams, for each incremental 0.025 inch deflection and for each of five samples (A–E) are set forth in the following table:

|           | A     | B      | C      | D      | E       |
|-----------|-------|--------|--------|--------|---------|
| 0.025 in. | 5 g.  | 5 g.   | 15 g.  | 20 g.  | 45 g.   |
| 0.050 in. | 10 g. | 10 g.  | 40 g.  | 75 g.  | 180 g.  |
| 0.075 in. | 15 g. | 20 g.  | 55 g.  | 125 g. | 500 g.  |
| 0.100 in. | 20 g. | 30 g.  | 100 g. | 170 g. | 770 g.  |
| 0.125 in. | 30 g. | 40 g.  | 195 g. | 270 g. | 970 g.  |
| 0.150 in. | 45 g. | 55 g.  |        | 390 g. | 1500 g. |
| 0.175 in. | 70 g. | 75 g.  |        |        | 1900 g. |
| 0.200 in. |       | 140 g. |        |        | 2600 g. |

The softest sample, sample A in the above table, is believed to represent about the most compliant, least resilient material desirable for use in a homogenous pad of the invention. Similarly, the hardest sample, sample E in the above table, is believed to represent about the least compliant, most resilient material desirable for use in the present invention. Therefore, although the invention is not necessarily limited to gelatinous elastomers with hardnesses ranging from sample A to sample E, such elastomers are considered more desirable for use in the present invention, with the most desirable material, sample C in the above table, corresponding to the material used in the Kitecko Ultrasound Standoff Pad of the preferred embodiment. Based upon the above-described measurements, it is anticipated that the gelatinous elastomer is sufficiently compliant when a compressive pressure between 100 grams per square inch and 3500 grams per square inch applied to the top surface of a thin strip of gelatinous elastomer will compress the height of the strip by approximately 25 percent. The preferred gelatinous elastomer shows such compression at approximately 380 grams per square inch.

Due to the absence of any established test to determine the hardness or softness of a gelatinous elastomer, it must be recognized that the above results are approximations reflecting the desirable range of physical properties and are expected to have a margin of error of at least 20%. Moreover, the physical characteristics described herein were found to be proportionally applicable to strips between 0.1 inches and 0.6 inches high. It is also expected that the above physical characteristics will be applicable proportionally to different-sized samples of the gelatinous elastomer which are not precisely 0.3 inches high, so long as the relative dimension of the different-sized samples are similar to the tested samples.

In the preferred embodiment of the present invention, the sealing pad 14 has a thin distortable membrane 24 which covers at least a portion of the gelatinous elastomer. This membrane is a smooth and regular external surface. In the preferred embodiment, the membrane is made from Tegaderm HP Transparent Wound Dressing manufactured by the 3M Corporation of St. Paul, Minn. and is formed to create a closed toroid which encloses the gelatinous elastomer in an air-tight manner. However, virtually any thin flexible film can be used for this membrane, including a film that forms on or as part of the surface of the gelatinous elastomer.

In an alternative embodiment, the sealing pad 14 is used without any membrane between the sealing pad 14 and the user's skin to take advantage of the physical characteristics of the gelatinous elastomer. For example, the previously described Kitecko Ultrasound Standoff Pad manufactured by 3M corporation is sufficiently tacky to adhere to the user's face. In another embodiment, an adhesive can be applied to the sealing pad 14. This allows the sealing pad 14 to maintain an air-tight seal between the user's face and the frame 12 with little or no pressure applied to the sealing pad 14.

The sealing pad 14 can be permanently attached to the frame 12 using any one of a number of commonly known techniques, such as adhesives or physical fasteners. Alternatively, the sealing pad 14 can be removably attached to the frame 12, allowing for easy replacement of the sealing pad 14 after it is worn or damaged, using various commonly known methods, such as the methods described below.

Figure 3:
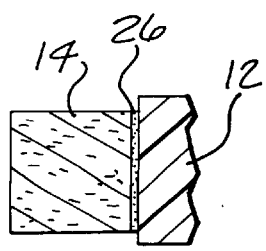
FIGS. 3–13 show partial cross sections of alternative embodiments of the goggle frame and seal suitable for use in the present invention taken along Line A-A' of FIG. 1.
Figure 9:
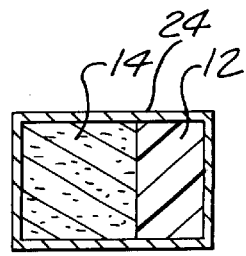
Figure 4:
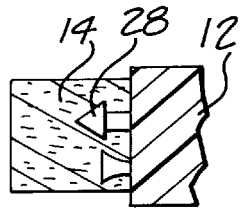
Figure 10:
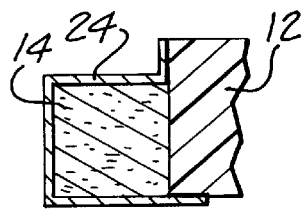
Figure 5:
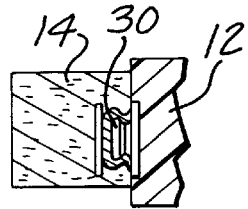
Figure 11:
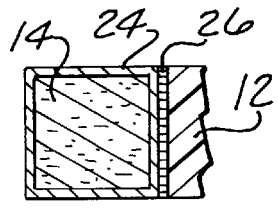
Figure 6:
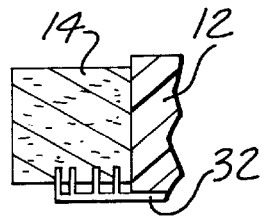
Figure 12:
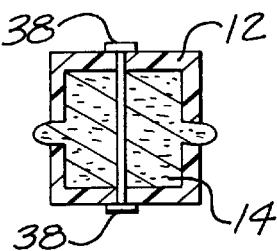
Figure 7:
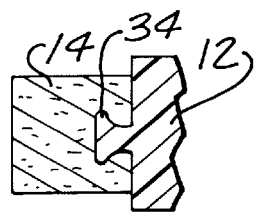
Figure 13:
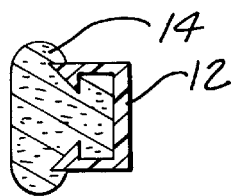
Figure 8:
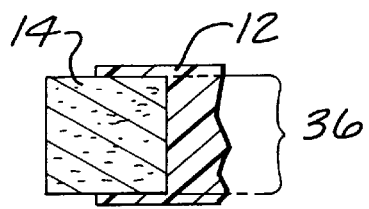
Figure 14:
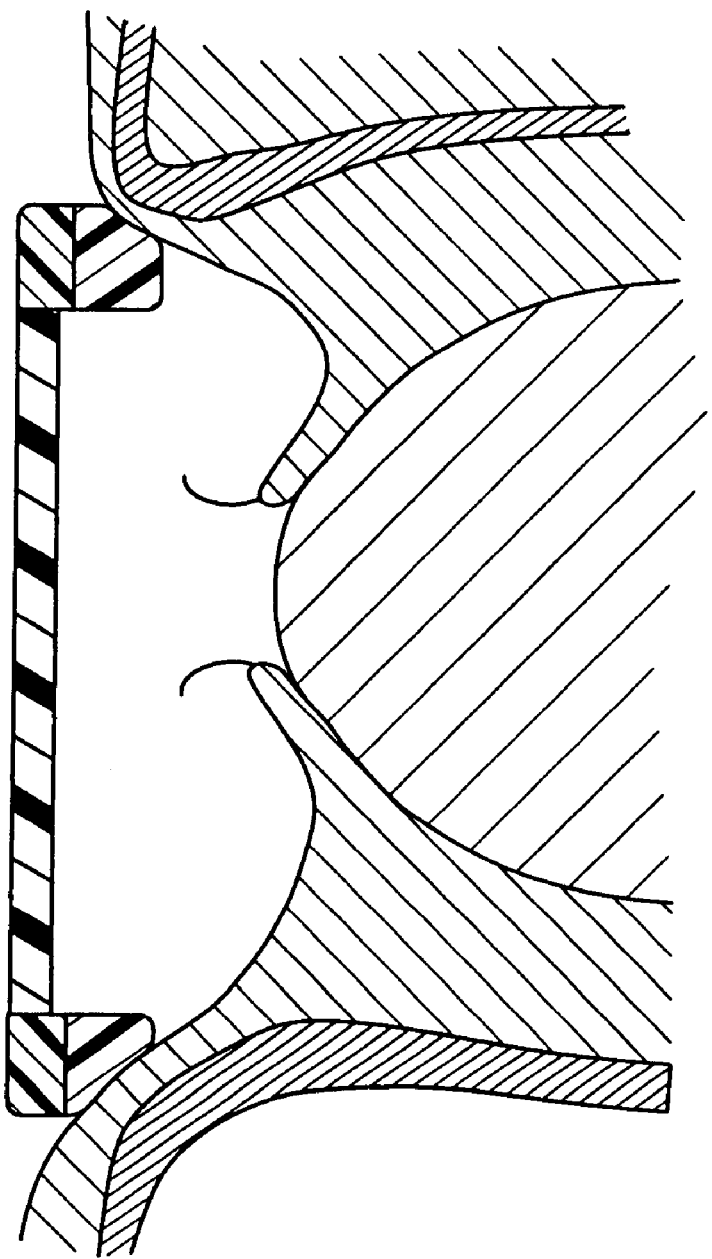
FIG. 14 shows a pictorial view of an alternative embodiment of the goggles in accordance with the present invention.

There are a multitude of means by which the sealing pad 14 can be permanently or removably attached to the frame 12. For example, the pad 14 can be glued, pasted, formed and cured, or attached with adhesives 26 onto the frame 12 as shown, for example, in FIG. 3. The pad 14 may also be attached using one or more pegs, anchors, screws or other fasteners 28 that are attached to the frame 12 and penetrate into the pad 14 as shown, for example, in FIG. 4. The pad 14 can also be attached to the frame 12 using interlocking molded forms, such as snaps 30, side projections 32, ziplock channels, or buttons 34 that are either attached to or are integral with the frame 12 and pad 14 as shown, for example, in FIGS. 5–7. The pad 14 may also fit into a slot or channel 36 in the frame 12 as shown, for example, in FIG. 8. The pad 14 may also be attached to the frame 12 by use of a membrane 24 which surrounds at least a portion of the frame 12 and a portion of the pad 14 as shown, for example, in FIG. 9. Likewise, a membrane 24 which either partially or fully surrounds the pad 14 can be attached to the frame 12 in numerous well known ways, including the use of screws, clamps, pegs, pins, glues, wires, paste, curing agents, snaps, buttons, anchors, or interlocking molded forms, as illustrated, for example, in FIGS. 10–11. The gelatinous elastomer of the pad 14 can also be squeezed or compressed between two portions of the frame 12, as illustrated, for example, in FIG. 12 using a screw 38 to squeeze the elastomer. The gelatinous elastomer can also be squeezed or fastened into a channel 36 as shown, for example, in FIG. 13.

In another alternative embodiment, the pliability or softness of the sealing pad 14 varies between the frame 12 and the user's face. For example, using well-known techniques of manufacturing silicone elastomers, the sealing pad 14 may be made softer or more pliable near the user's face and be made to increase in hardness and become less pliable closer to the frame 12. This alternative embodiment can be used to provide for a very soft and flexible portion of the pad 14 near the user's face while ensuring that the pad as a whole is not so deformable as to allow the frame 12 to impinge upon the user's face.

The sealing pad 14 described in this invention can be used in other situations where it is desirable to form a substantially air-tight seal with the user's skin. For example, the sealing pad 14 of this invention can be used on breathing masks and other apparatus designed to isolate any portion or portions of the user's face from the outside environment. Likewise, the sealing pad 14 of this invention may be used to form an air-tight or water-tight seal between the user's skin and protective clothing or garments. In such cases, the sealing pad 14 may be forced against the skin by the mask or garment or the sealing pad 14 may be sufficiently tacky to adhere to the user's skin once it is initially conformed to the skin.

The embodiments of the invention in which an exclusive property or privilege is claimed are defined as follows:

1. Goggles for isolation of a user's eyes from the outside environment comprising:

a frame including a transparent portion adapted to cover at least one of the user's eyes;

a sealing pad adjacent to the frame, said sealing pad comprising a compliant and resiliently deformable gelatinous elastomer suitable to conform under pressure to form a substantially airtight seal between the frame and at least a portion of the user's face adjacent to the sealing pad; and an attachment means for removable attachment of the sealing pad to the frame.

2. Goggles for isolation of a user's eyes from the outside environment comprising:

a flexible frame consisting of a thin sheet of transparent material which conforms generally, to the shape of the user's face and is adapted to cover at least one of the user's eyes; and a sealing pad adjacent to the frame said sealing pad comprising a compliant and resiliently deformable gelatinous elastomer suitable to conform under pressure to form a substantially airtight seal between the frame and at least a portion of the user's face adjacent to the sealing pad.

* * * * *